United States Patent
Yeh et al.

(10) Patent No.: US 12,213,762 B2
(45) Date of Patent: Feb. 4, 2025

(54) SOLE DATA COLLECTION DEVICE AND SOLE DATA COLLECTION METHOD

(71) Applicant: Chang Gung University, Taoyuan (TW)

(72) Inventors: Ting-Ting Yeh, Taoyuan (TW); Miao-Yu Liao, Taoyuan (TW); Chia-Chih Chang, Taoyuan (TW); Yu-Syuan Chen, Taoyuan (TW); I-Feng Hsu, Taoyuan (TW)

(73) Assignee: Chang Gung University, Taoyuan (TW)

( * ) Notice: Subject to any disclaimer, the term of this patent is extended or adjusted under 35 U.S.C. 154(b) by 188 days.

(21) Appl. No.: 18/128,393

(22) Filed: Mar. 30, 2023

(65) Prior Publication Data

US 2023/0320589 A1    Oct. 12, 2023

Related U.S. Application Data

(60) Provisional application No. 63/328,748, filed on Apr. 8, 2022.

(51) Int. Cl.
*A61B 5/00* (2006.01)
*A61B 5/01* (2006.01)
*G06T 7/00* (2017.01)

(52) U.S. Cl.
CPC .............. *A61B 5/0035* (2013.01); *A61B 5/01* (2013.01); *A61B 5/4041* (2013.01); *A61B 5/7267* (2013.01); *A61B 5/742* (2013.01); *G06T 7/0012* (2013.01)

(58) Field of Classification Search
CPC ... A61B 5/0035; A61B 5/4041; A61B 5/7267; A61B 5/742
See application file for complete search history.

(56) References Cited

U.S. PATENT DOCUMENTS

| 2019/0021649 A1 | 1/2019 | Van Snellenberg et al. |
| 2023/0226759 A1* | 7/2023 | Dunning ............... B29C 64/188 |
| | | 264/241 |

FOREIGN PATENT DOCUMENTS

| CN | 208974118 U | 6/2019 |
| TW | 201609055 A | 3/2016 |

OTHER PUBLICATIONS

Lawrence A Lavery et al., Preventing diabetic foot ulcer recurrence in high-risk patients: use of temperature monitoring as a self-assessment tool, Diabetes Care, 2007, vol. 30, No. 1.

* cited by examiner

*Primary Examiner* — Gerald Johnson
(74) *Attorney, Agent, or Firm* — Locke Lord LLP; Tim Tingkang Xia, Esq.

(57) ABSTRACT

A sole data collection device and a sole data collection method are disclosed. The sole data collection device includes an image capture module, a temperature detection module and a monofilament testing module. The sole data collection device is used for collecting the sole data of a user, and the sole data is transmitted to a cloud server. The sole data collection device and the sole data collection method are not only convenient for a user to collect sole data at home at any time, but also allow the user's caregiver and/or relevant medical care personnel to extract the sole data from the cloud server to screen the user's plantar condition, so as to solve the problem that it is time-consuming and costly to go to a medical institution for relevant examinations.

10 Claims, 12 Drawing Sheets

SOLE DATA COLLECTION DEVICE AND SOLE DATA COLLECTION METHOD

REFERENCE TO RELATED APPLICATIONS

The present application is based on, and claims priority from, U.S. Provisional Application No. 63/328,748 filed Apr. 8, 2022, the disclosure of which is hereby incorporated by reference herein in its entirety.

FIELD OF THE INVENTION

The present invention relates to a field of data collection, and more particularly, to a sole data collection device and a sole data collection method.

BACKGROUND OF THE INVENTION

According to statistics from the International Diabetes Federation (IDF), the global population with diabetes is increasing at a rate of 10 million per year. In 2021, the total number of people with diabetes in the world is 463 million, accounting for 6.6% of the total population. About 25% of diabetic patients will have diabetic foot. 60% of diabetic foot may be complicated by cellulitis due to poor wound care, and nearly 20% of diabetic feet may result in amputation. Statistics show that the mortality rate after amputation is as high as 40% within three years, and as high as 70% within five years.

In order to confirm whether a patient has a diabetic foot, the patient needs to go to a hospital or clinic and other medical places for relevant examinations. According to the content of "retinopathy, neuropathy and foot care" (American Diabetes Association Professional Practice Committee; 12. Retinopathy, Neuropathy, and Foot Care: Standards of Medical Care in Diabetes—2022. Diabetes Care 1 Jan. 2022; 45 (Supplement 1): S185-S194. https://doi.org/10.2337/dc22-S012) in the 2022 diabetes clinical guidelines issued by the American Diabetes Association, it is set forth that foot examination should include skin examination, evaluation of foot deformities, neurological evaluation, and vascular evaluation including leg and foot pulses, so as to confirm whether the patient has a diabetic foot. Neurological examination includes monofilament testing, in cooperation with at least one of acupuncture, temperature, or vibration testing. However, it is time-consuming for patients to go to medical institutions for examination, and it is impossible to evaluate the condition of the patient's soles instantly. Accordingly, the inventor of the present invention hope to solve these problems for the conditions of the soles of the patient's feet to be evaluated instantly and for the cost of time spent by patients on medical visits to be reduced.

SUMMARY OF THE INVENTION

The primary object of the present invention is to provide a sole data collection device and sole data collection method to solve the problem that it is time-consuming to go to a medical institution for relevant examinations and cannot be screened immediately.

The sole data collection device, comprising a box, the box including a data collection plate and a back plate, the data collection plate being arranged correspondingly to the back plate; the data collection plate including a transparent plate and a plurality of openings, the plurality of openings being arranged on the data collection plate and corresponding in position to a great toe, a first metatarsal bone, a third metatarsal bone, a fifth metatarsal bone, a midfoot and a heel of a left foot and a right foot of a user; the box including a control module, a power supply module, a moving apparatus, an image capture module, a temperature detection module and a monofilament testing module therein, the control module being coupled to the power supply module, the moving apparatus, the image capture module, the temperature detection module and the monofilament testing module; temperature detection position data and monofilament testing position data being stored in the control module in advance; the control module being configured to communicate with an external device a cloud server; the image capture module being arranged on an inner surface of the back plate of the box and corresponding in position to the transparent plate; the moving apparatus being arranged on an inner surface of the box, the temperature detection module and the monofilament testing module being arranged on the moving apparatus, the control module controlling the moving apparatus to move the temperature detection module and the monofilament testing module according to the temperature detection position data and the monofilament testing position data.

In one embodiment of the present invention, the sole data collection device further comprises a support handle, the support handle including a first rod, a second rod and a third rod, one end of the first rod being rotatably connected to one side of the box, one end of the second rod being rotatably connected to another side of the box, one end of the third rod being fixedly connected to another end of the first rod, another end of the third rod being fixedly connected to another end of the second rod, wherein when the third rod is located between an outer surface of the back plate of the box and a ground and one side of the third rod is in contact with the ground, an included angle is defined between an imaginary plane parallel to the data collection plate and the ground, and the included angle is 15-35 degrees, preferably, the included angle is 15-25 degrees.

In one embodiment of the present invention, a first holding member is provided on the one side of the box, and the first holding member is located on a rotation path of the first rod; a second holding member is provided on the another side of the box, and the second holding member is located on a rotation path of the second rod; wherein when the first rod is held by the first holding member, the second rod is held by the second holding member, and the one side of the third rod is in contact with the ground, an included angle is defined between the imaginary plane and the ground, and the included angle is 15-35 degrees, preferably, the included angle is 15-25 degrees.

In one embodiment of the present invention, when the back plate is in contact with the ground, an included angle is defined between an imaginary plane parallel to the data collection plate and the ground, and the included angle is 15-35 degrees, preferably, the included angle is 15-25 degrees.

In one embodiment of the present invention, the monofilament testing module includes a third motor, a second slider, a monofilament and a fourth slide rail, a gear is provided on the third motor, the second slider is arranged on the fourth slide rail, one end of the monofilament is connected to one end of the second slider facing the data collection plate, a rack is provided on one side of the second slider facing the gear, the gear is meshed with the rack, the fourth slide rail is perpendicular to the data collection plate, and another end of the monofilament is perpendicular to the data collection plate.

In one embodiment of the present invention, the control module includes a processor, a storage module and a first transmission module, wherein the processor is configured to receive and transmit the data transmitted by the image capture module, the temperature detection module and the monofilament testing module and to control the moving apparatus, the image capture module, the temperature detection module and the monofilament testing module, wherein the storage module is configured to store the data received by the processor, and the storage module stores the temperature detection position data and the monofilament testing position data in advance for the processor to extract the data stored in the storage module.

In one embodiment of the present invention, the external device includes an application program, a second transmission module and a display module, the external device interacts with the sole data collection device and the cloud server via the application program, the external device controls the sole data collection device via the application program, the external device communicates with the sole data collection device and the cloud server via the second transmission module to receive the data transmitted by the sole data collection device or the cloud server, or to transmit data to the sole data collection device or the cloud server; the display module is configured to display the data in the external device.

The sole data collection method, comprising a device providing step, an image capturing step, an image analysis step, a comparison analysis step, a temperature detection step, a monofilament testing step and an inquiry reply step. The device providing step: providing the aforementioned sole data collection device. The image capturing step: the image capture module capturing a sole image to obtain image data and transmitting the image data to the control module. The image analysis step: the control module transmitting the image data to an image analysis module for analysis to identify whether the image data includes a wound image, if the identified image data includes the wound image, the area where the wound image in the image data is located being marked to obtain image analysis result data; if the identified image data does not include the wound image, the image data serving as the image analysis result data. The comparison analysis step: the image analysis module transmitting the image analysis result data to a comparison analysis module, the comparison analysis module comparing the image analysis result data and the monofilament testing position data to determine whether each monofilament testing position overlaps with the marked area, if it is determined that there is an overlap, skip testing message data being generated and the skip testing message data being transmitted to the control module. The temperature detection step: the control module controlling the moving apparatus to move the temperature detection module to each temperature detection position according to the temperature detection position data, the temperature detection module performing temperature detection at each temperature detection position to obtain corresponding temperature data, the corresponding temperature data being transmitted to the control module, the control module transmitting the corresponding temperature data to the external device or the cloud server. The monofilament testing step: the control module controlling the moving apparatus to move the monofilament testing module to each monofilament testing position according to the monofilament testing position data, the monofilament testing module performing monofilament testing at each monofilament testing position, after completing the monofilament testing, the control module recording the current monofilament testing position to obtain corresponding monofilament testing data, the control module transmitting the corresponding monofilament testing data to the external device or the cloud server; wherein if the control module receives the skip testing message data, the control module controls the moving apparatus to skip the monofilament testing position overlapping with the marked area. The inquiry reply step, after receiving the corresponding monofilament testing data, the external device generating corresponding inquiry message data and displaying the inquiry message data on the external device, the external device replying to the inquiry message data to obtain corresponding reply message data, the external device transmitting the reply message data to the cloud server, wherein the inquiry message data is to inquire the user's plantar sensation; wherein the image analysis module is stored in the external device or the cloud server; wherein the comparison analysis module is stored in the external device or the cloud server.

In one embodiment of the present invention, the skip testing message data is to instruct the control module to control the moving apparatus to skip the monofilament testing position overlapping with the marked area.

In one embodiment of the present invention, the sole data collection method further comprises a temperature comparison step after the temperature detection step, in the temperature comparison step, the temperature comparison module comparing each of the temperature data, if a temperature difference recorded in any two of the temperature data is greater than 2.2° C., temperature warning data being generated, wherein the temperature comparison module is stored in the external device or the cloud server.

To sum up, the sole data collection device and the sole data collection method provided by the present invention can solves the problem that it is time-consuming to go to a medical institution for relevant examinations and cannot be screened immediately.

DETAILED DESCRIPTION OF THE PREFERRED EMBODIMENTS

Figure 1:
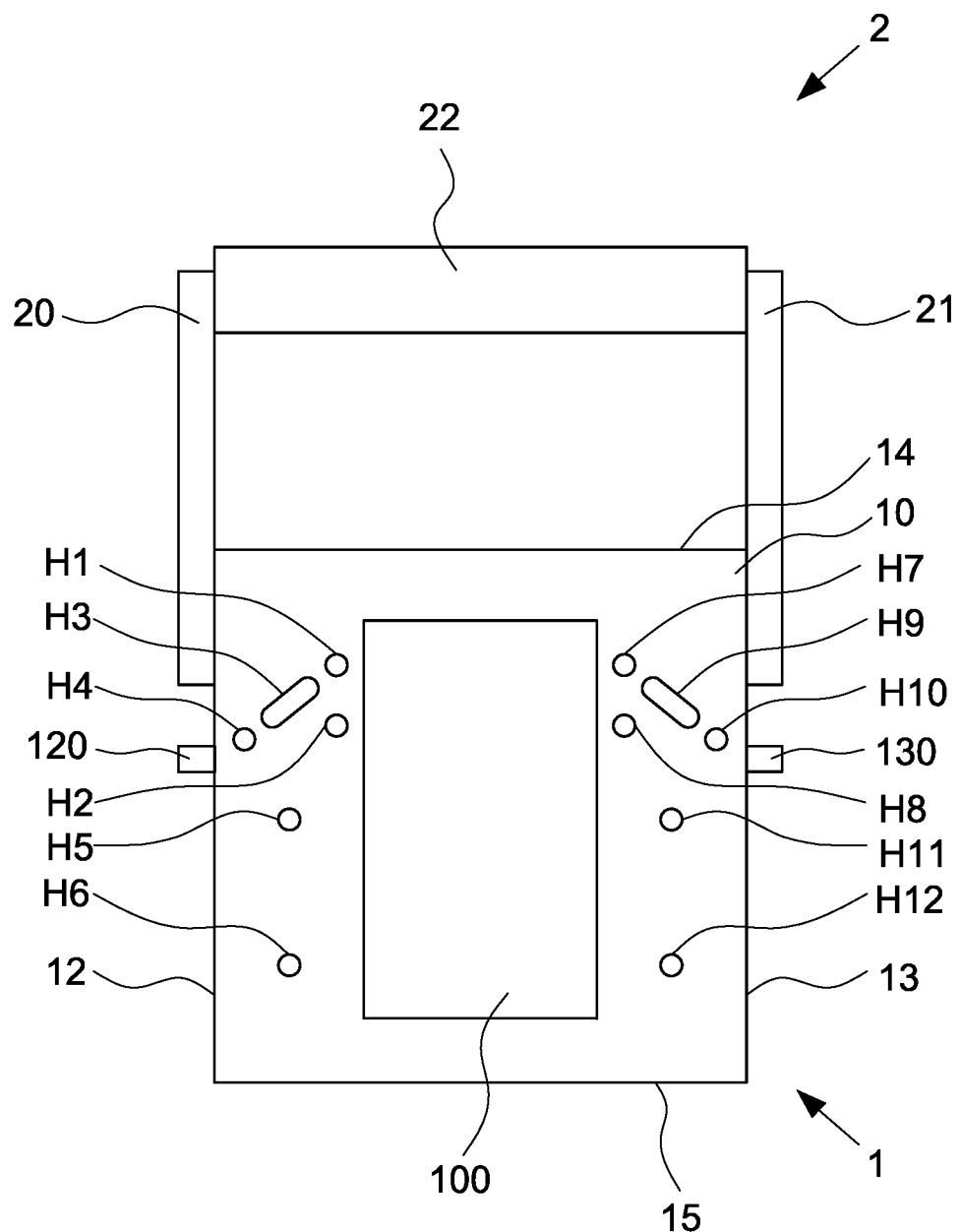
FIG. 1 is a schematic top view of the sole data collection device according to one embodiment.

Embodiments of the present invention will now be described, by way of example only, with reference to the accompanying drawings.

Spatially relative terms, such as "upper," "lower," "left," "right," and the like, may be used herein for ease of explanation to describe one element or feature's relationship to another element(s) or feature(s) as illustrated in the figures. It will be understood that the spatially relative terms are intended to encompass different orientations of the device in use or in operation, in addition to the orientation depicted in the figures. In addition, the terms "first," "second," "third," "fourth," and the like, are only used for descriptive purposes, and should not be construed as indicating or implying relative importance or implying the number of indicated technical features.

In the description of the specification, terms such as "one embodiment", "some embodiments", "another embodiments" or "example" are intended to indicate that specific features, structures, materials or characteristics related to the embodiment(s) or example(s) are included in at least one embodiment or example of the present disclosure.

In the embodiments of the present invention, the "outer surface" refers to the surface located on the outside of the box, and the "inner surface" refers to the surface facing the inside of the box.

Referring to FIG. 1, FIG. 2, FIG. 3, FIG. 4, FIG. 5 and FIG. 6, the present invention provides a sole data collection device, comprising a box 1. The box 1 includes a data collection plate 10, a back plate 11, a left side plate 12, a right side plate 13, an upper side plate 14, and a lower side plate 15. The data collection plate 10 is arranged correspondingly to the back plate 11. The left side plate 12 is arranged correspondingly to the right side plate 13. The upper side plate 14 is arranged correspondingly to the lower side plate 15. In one embodiment of the present invention, the box 1 is in the shape of a cuboid, and the inside of the box 1 is hollow. In another embodiment of the present invention, the box 1 is in the shape of a quadrangular truncated pyramid, but not limited to this in actual implementation. The box 1 may be in other shapes. The present invention does not particularly limit the shape of the box 1. The box 1 is not limited to a closed structure. The box 1 may be an open structure, for example, the upper side plate 14 may be removed from the box 1, or the left side plate 12 and the right side plate 13 of the box 1 are formed with heat emission holes, so that the inside of the box 1 can communicate with the outside.

Figure 3:
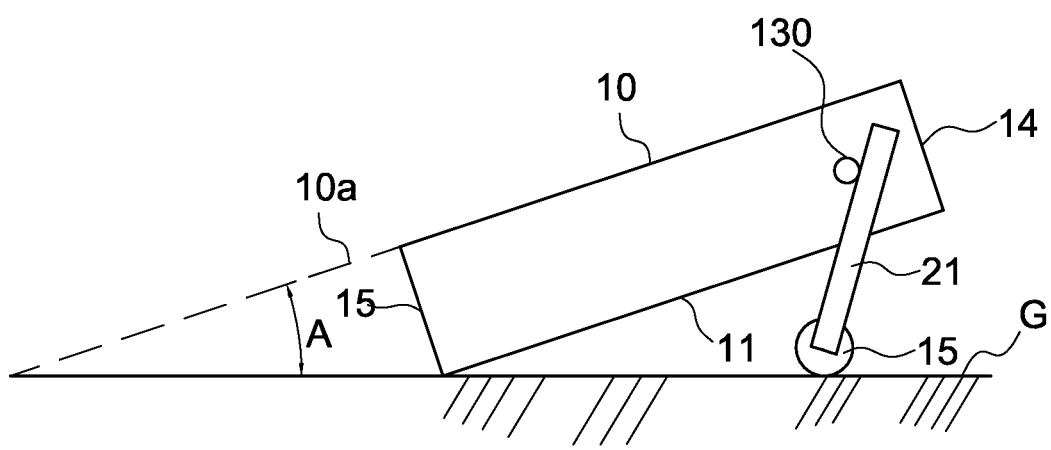
FIG. 3 is a schematic side view of an included angle defined between the imaginary plane extending from the data collection plate of the sole data collection device and the ground according to one embodiment of the present invention.

Referring to FIG. 1 and FIG. 3, in one embodiment of the present invention, the sole data collection device further comprises a support handle 2. The support handle 2 is configured to adjust the height of the box 1. The user may hold the support handle 2 to lift and move the box 1. The support handle 2 includes a first rod 20, a second rod 21, and a third rod 22. One end of the first rod 20 is rotatably connected to the left side plate 12 of the box 1. One end of the second rod 21 is rotatably connected to the right side plate 13 of the box 1. One end of the third rod 22 is fixedly connected to the other end of the first rod 20. The other end of the third rod 22 is fixedly connected to the other end of the second rod 21. Therefore, the third rod 22 can rotate with one end of the first rod 20 and one end of the second rod 21 as the rotation center. In one embodiment of the present invention, the length of the first rod 20 is the same as that of the second rod 21. In one embodiment of the present invention, the rotational connection may be achieved by means of a bearing, but not limited to this in actual implementation. It may be achieved by other rotating parts. In one embodiment of the present invention, the fixed connection may be achieved by means of screws, but not limited to this in actual implementation. It may be achieved by other fixing parts.

Referring to FIG. 1 and FIG. 3, in one embodiment of the present invention, when the user wants to carry and move the sole data collection device, he/she can hold the third rod 22 of the support handle 2 to lift the box 1 and move it. When the user wants to use the sole data collection device to collect sole data, the first rod 20 and the second rod 21 are rotated for the third rod 22 to be located between the outer surface of the back plate 11 of the box 1 and the ground G, and one side of the third rod 22 is in contact with the ground G. At this time, an imaginary plane 10*a* extends from the data collection plate 10 of the box 1. The imaginary plane 10*a* is parallel to the data collection plate 10. The imaginary plane 10*a* intersects the ground G to form an included angle A. Then, the user sits on a seat and places the sole of the foot on the outer surface of the data collection plate of the box 1 for collecting sole data. The included angle A is 15-35 degrees, preferably 15-25 degrees, so that when the sole of the user's foot is placed on the outer surface of the data collection plate 10 of the box 1, the user's foot is in a relaxed state to prevent the user's foot from getting tight to affect the data collected by the sole data collection device. If the user's foot gets tight, the data collected by the sole data collection device cannot reflect the user's plantar conditions accurately.

Figure 2:
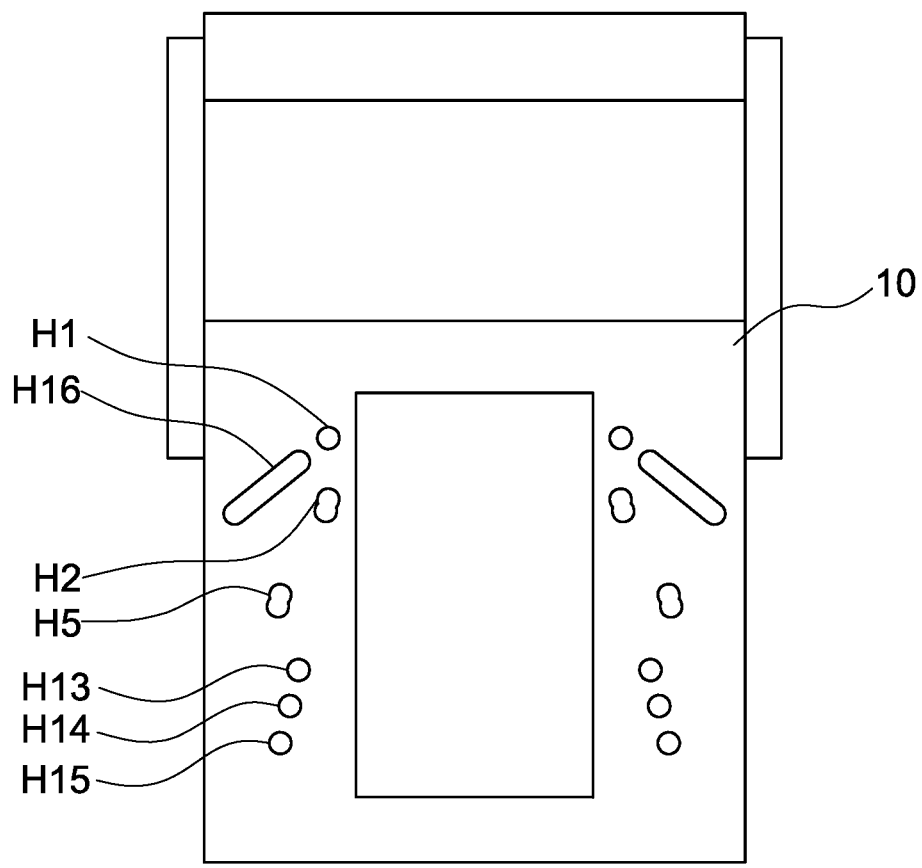
FIG. 2 is a schematic top view of the sole data collection device according to another embodiment.

Referring to FIG. 1, FIG. 2 and FIG. 3, a first holding member 120 is provided on the outer surface of the left side plate 12 of the box 1, and the first holding member 120 is located on the rotation path of the first rod 20. A second holding member 130 is provided on the outer surface of the right side plate 13 of the box 1, and the second holding member 130 is located on the rotation path of the second rod 21. The first holding member 120 is configured to hold the first rod 20, and the second holding member 130 is configured to hold the second rod 21. When the first rod 20 is held by the first holding member 120, the second rod 21 is held by the second holding member 130, and one side of the third rod 22 is in contact with the ground G, an imaginary plane 10*a* extends from the data collection plate 10 of the box 1 towards the ground G. The imaginary plane 10*a* is parallel to the data collection plate 10. The imaginary plane 10*a* intersects the ground G to form an included angle A. The included angle A is 15-35 degrees, preferably 15-25 degrees. Both the first holding member 120 and the second holding member 130 are screws, but not limited to this in actual implementation. They may be other types of holding parts used to hold the first rod 20 and the second rod 21. In another embodiment of the present invention, the first holding member 120 and the second holding member 130 are not provided. One side of the third rod 22 is in contact with the ground G, and the other side of the third rod 22 is in contact with the outer surface of the back plate 11 of the box 1. An imaginary plane 10*a* extends from the data collection plate 10 of the box 1 towards the ground G. The imaginary plane 10*a* is parallel to the data collection plate 10. The imaginary plane 10*a* intersects the ground G to form an included angle A. The included angle A is 15-35 degrees, preferably 15-25 degrees.

Figure 4:
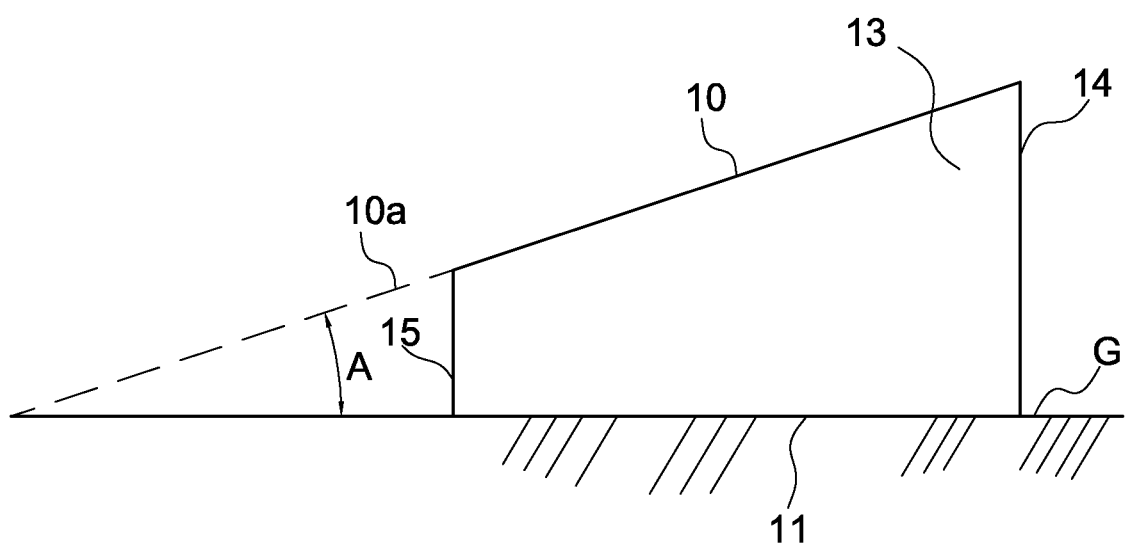
FIG. 4 is a schematic side view of an included angle defined between the imaginary plane extending from the data collection plate of the sole data collection device and the ground according to another embodiment of the present invention.

Referring to FIG. 1 and FIG. 4, in another embodiment of the present invention, when the back plate 11 is in contact with the ground G, an imaginary plane 10*a* extends from the data collection plate 10 towards the ground G. The imaginary plane 10*a* is parallel to the data collection plate 10. The imaginary plane 10*a* intersects the ground G to form an included angle A. The included angle A is 15-35 degrees. In order to make the imaginary plane 10*a* extending from the data collection plate 10 intersect with the ground G to form the included angle A, the left side plate 12 and the right side plate 13 of the box 1 may be in the same right-angled trapezoid shape. The left side of the data collection plate 10 is connected to the hypotenuse of the left side plate 12, and the right side of the data collection plate 10 is connected to the hypotenuse of the right side plate 13. The imaginary plane 10*a* extends from the data collection plate 10. The imaginary plane 10*a* intersects the ground G to form the included angle A. Then, the user sits on a seat and places the sole of the foot on the outer surface of the data collection plate 10 of the box 1 for collecting sole data. The included angle A is 15-35 degrees, preferably 15-25 degrees. The above is just an example, and the actual implementation is not limited to this. The left side plate 12 and the right side plate 13 may be in the shape of an isosceles trapezoid or other trapezoids. The configuration of the box 1 may be other configurations that enable the imaginary plane 10 a extending from the data collection plate 10 to intersect the ground G to form the included angle A. In addition, the box 1 may be further provided with a movable handle, so that the user can move the box 1 using the movable handle. For example, the movable handle may be arranged at the center of the lower side plate 15 of the box 1. The user can lift the box 1 by pulling the movable handle, so as to carry and move the box 1.

Referring to FIG. 1 and FIG. 2, the data collection plate 10 of the sole data collection device includes a transparent plate 100 and a plurality of openings. The plurality of openings are arranged on the data collection plate 10 and correspond in position to the great toe, the first metatarsal bone, the third metatarsal bone, the fifth metatarsal bone, the midfoot and the heel of the user's left and right feet. In one embodiment of the present invention, the transparent plate 100 is a transparent glass plate, but not limited to this in actual implementation. The transparent plate 100 may be a plate made of transparent materials, such as a transparent plastic plate. The opening corresponding to the great toe of the left foot is defined as a first opening H1. The opening corresponding to the first metatarsal bone of the left foot is defined as a second opening H2. The opening corresponding to the third metatarsal bone of the left foot is defined as a third opening H3. The opening corresponding to the fifth metatarsal bone of the left foot is defined as a fourth opening H4. The opening corresponding to the midfoot of the left foot is defined as a fifth opening H5. The opening corresponding to the heel of the left foot is defined as a sixth opening H6. The opening corresponding to the great toe of the right foot is defined as a seventh opening H7. The opening corresponding to the first metatarsal bone of the right foot is defined as an eighth opening H8. The opening corresponding to the third metatarsal bone of the right foot is defined as a ninth opening H9. The opening corresponding to the fifth metatarsal bone of the right foot is defined as a tenth opening H10. The opening corresponding to the midfoot of the right foot is defined as an eleventh opening H11. The opening corresponding to the heel of the right foot is defined as a twelfth opening H12. The foregoing content is only used to illustrate the technical content of the present invention, but not limited to this in actual implementation. In response to differences in the length and width of the soles of different users, more openings may be further provided. For example, the data collection plate 10 may be formed with additional openings corresponding in position to the heel of a user with a sole length of 180 mm, 220 mm, or 255 mm. These openings are defined as a thirteenth opening H13, a fourteenth opening H14, and a fifteenth opening H15. Therefore, the data collection plate 10 has three openings corresponding in position to the heel of the left foot. In addition, each opening is not limited to being an independent opening. The openings may be connected to each other to form the same opening. For example, the third opening H3 and the fourth opening H4 in FIG. 1 may be connected to form the sixteenth opening H16 in FIG. 2. In addition, the shape of each opening is not particularly limited. For example, as shown in FIG. 2, the first opening H1, the thirteenth opening H13, the fourteenth opening H14 and the fifteenth opening H15 are all circular; the second opening H2 and the fifth opening H5 are peanut-shaped; and the sixteenth opening H16 is a rounded rectangle, but not limited to this in actual implementation. Each opening may be in other shapes, such as rectangle, ellipse or triangle.

Figure 5:
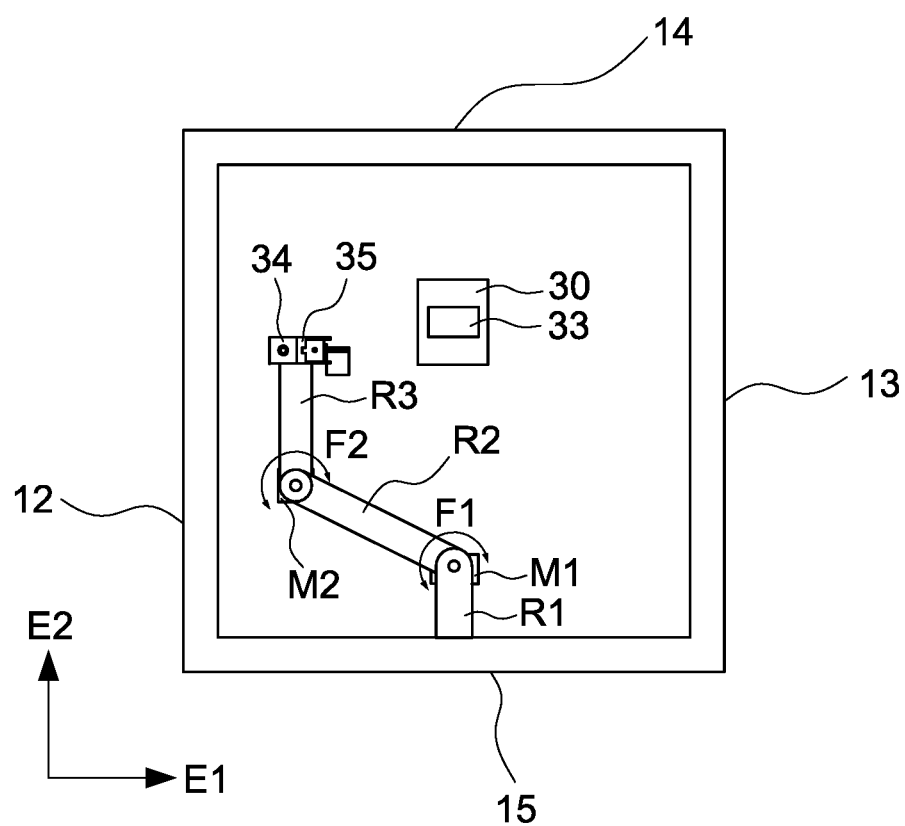
FIG. 5 is a schematic top view of the moving apparatus, the temperature detection module, the monofilament testing module and the image capture module inside the box of the foot data collection device according to one embodiment of the present invention.
Figure 7:
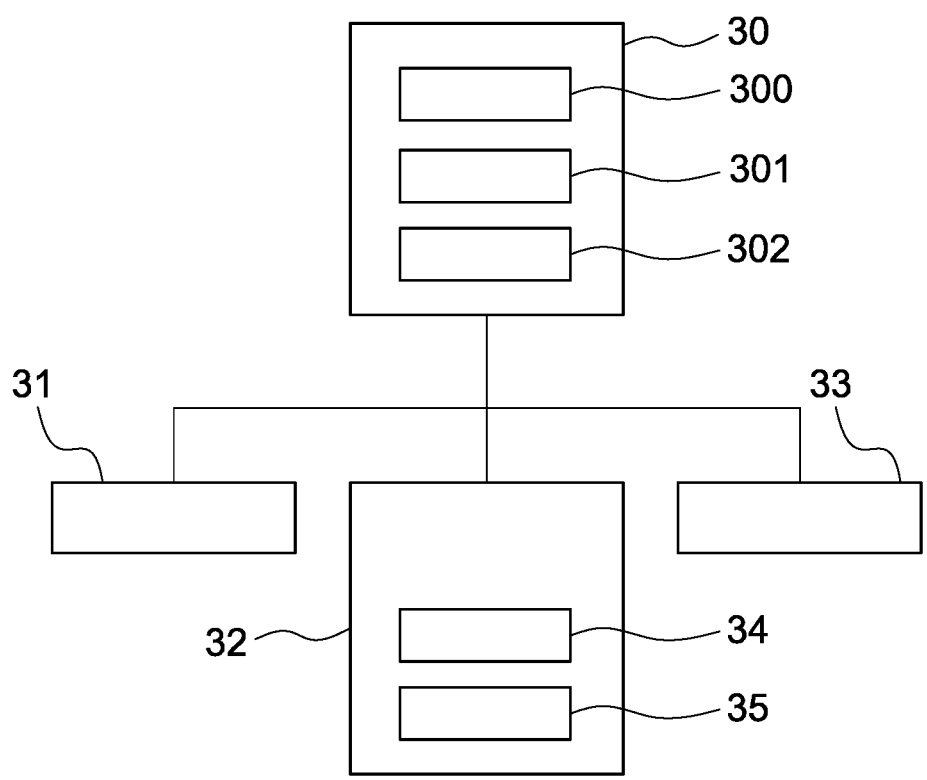
FIG. 7 is a schematic diagram of the system architecture in the sole data collection device.

Referring to FIG. 5 and FIG. 7, in one embodiment of the present invention, the box 1 includes a control module 30, a power supply module 31, a moving apparatus 32, an image capture module 33, a temperature detection module 34 and a monofilament testing module 35 therein. The control module 30 is coupled to the power supply module 31, the moving apparatus 32, the image capture module 33, the temperature detection module 34 and the monofilament testing module 35. Temperature detection position data and monofilament testing position data are stored in the control module 30 in advance. The power supply module 31 is configured to supply power to the control module 30, the moving apparatus 32, the image capture module 33, the temperature detection module 34 and the monofilament testing module 35. The image capture module 33 is arranged on the inner surface of the back plate 11 of the box 1 and corresponds in position to the transparent plate 100. When the user places his/her sole on the outer surface of the transparent plate 100, the image capture module 33 captures images of the sole of the user's foot to obtain image data, and transmits the image data to the control module 30. The temperature detection position data includes the data of each temperature detection position and the data of the order of movement to each temperature detection position. The monofilament testing position data includes the data of each monofilament testing position and the data of the order of movement to each monofilament testing position. The order of movement may be a preset order or a random order. The preset order is the order set in advance. The random order is the order obtained by randomly arranging the preset order. The moving apparatus 32 is arranged on the inner surface of the box 1. The temperature detection module 34 and the monofilament testing module 35 are arranged on the moving apparatus 32. The control module 30 controls the moving apparatus 32 to move according to the temperature detection position data and the monofilament testing position data for the temperature detection module 34 to be moved to each temperature detection position or for the monofilament testing module 35 to be moved to each monofilament testing position. The temperature detection module 34 performs temperature detection at each temperature detection position to obtain corresponding temperature data, and then transmits the temperature data to the control module 30. The monofilament testing module 35 performs the monofilament testing at each monofilament testing position, and the control module 30 records the current monofilament testing position after the monofilament testing is completed, so as to obtain the corresponding monofilament testing data.

Referring to FIG. 1, FIG. 5, FIG. 6 and FIG. 7, in one embodiment of the present invention, the temperature detection positions correspond to the first opening H1, the second opening H2, the third opening H3, the fourth opening H4, the fifth opening H5, the sixth opening H6, the seventh opening H7, the eighth opening H8, the ninth opening H9, the tenth opening H10, the eleventh opening H11 and the twelfth opening H12, respectively. The monofilament testing positions correspond to the first opening H1, the second opening H2, the third opening H3, the fourth opening H4, the seventh opening H7, the eighth opening H8, the ninth opening H9, and the tenth opening H10, respectively. The control module 30 controls the moving apparatus 32 to move according to the temperature detection position data for the temperature detection module 34 to be moved to each temperature detection position. The control module 30 controls the monofilament testing module 35 to move to each monofilament testing position according to the monofilament testing position data. The temperature detection positions and the monofilament testing positions are all located on a virtual coordinate plane parallel to the data collection plate and the back plate 11. The virtual coordinate plane is located between the data collection plate 10 and the back plate 11. The virtual coordinate plane defines a first direction E1 and a second direction E2. The first direction E1 is perpendicular to the second direction E2. The first direction E1 is defined as the X-axis direction, and the second direction E2 is defined as the Y-axis direction. The temperature detection position data includes the data of each temperature detection position, that is, the coordinates of each temperature detection position corresponding to the virtual coordinate plane. The monofilament testing position data includes the data of each monofilament testing position, that is, the coordinates of each monofilament testing position corresponding to the virtual coordinate plane. Therefore, the control module 30 controls the moving apparatus 32 to move to the specified coordinates according to the temperature detection position data and the monofilament testing position data, so that the temperature detection module 34 is moved to each temperature detection position, and the monofilament testing module 35 is moved to each monofilament testing position.

Referring to FIG. 7, the power supply module 31 is a dry battery. The dry battery may be a disposable battery or a rechargeable battery.

Referring to FIG. 1, FIG. 5 and FIG. 7, in one embodiment of the present invention, the moving apparatus 32 is an electric robotic arm, including a first arm R1, a first motor M1, a second arm R2, a second motor M2 and a third arm R3. One end of the first arm R1 is fixedly connected to the inner surface of the lower side plate 15 of the box 1. The other end of the first arm R1 is connected to one end of the second arm R2 via the first motor M1. The other end of the second arm R2 is connected to one end of the third arm R3 via the second motor M2. The temperature detection module 34 and the monofilament testing module 35 are arranged at the other end of the third arm R3. The first motor M1 is configured to swing the second arm R2 around the first motor M1 along a first swing direction F1. The second motor M2 is configured to swing the third arm R3 around the second motor M2 along a second swing direction F2. Both the first swing direction F1 and the second swing direction F2 are located on the virtual coordinate plane. Therefore, the moving apparatus 32 can move the temperature detection module 34 to each temperature detection position and the monofilament testing module 35 to each monofilament testing position, but not limited to this in actual implementation. The moving apparatus 32 may be a pneumatic robotic arm or a hydraulic robotic arm. The structure of the moving apparatus 32 is not limited to that described in this embodiment. It may be a three-axis robotic arm, a four-axis robotic arm, a five-axis robotic arm, or a six-axis robotic arm. The moving apparatus 32 may move in a third direction. The third direction is perpendicular to the first direction E1, and the third direction is also perpendicular to the second direction E2. The third direction is defined as the Z-axis, so as to adjust the positions of the temperature detection module 34 and the monofilament testing module 35 more flexibly. In one embodiment of the present invention, the first motor M1 and the second motor M2 are servo motors, but not limited to this in actual implementation. They may be different types of motors, such as DC motors, AC motors, or stepping motors.

Referring to FIG. 4 and FIG. 7, in another embodiment of the present invention, the moving apparatus 32 may be an electric XY table, including a first slide rail SR1, a second slide rail SR2, a third slide rail SR3 and a first slider SB. The first slide rail SR1 is arranged on the inner surface of the left side plate 12. The second slide rail SR2 is arranged on the inner surface of the right side plate 13. The first slide rail SR1 and the second slide rail SR2 are parallel to each other. The direction of the first slide rail SR1 and the direction of the second slide rail SR2 are parallel to the second direction E2. One end of the third slide rail SR3 is disposed on the first slide rail SR1. The other end of the third slide rail SR3 is disposed on the second slide rail SR2. The third slide rail SR3 is perpendicular to the first slide rail SR1 and the second slide rail SR2. The direction of the third slide rail SR3 is parallel to the first direction E1. The third slide rail SR3 can slide on the first slide rail SR1 and the second slide rail SR2, that is, the third slide rail SR3 can move along the first direction E1. The first slider SB is disposed on the third slide rail SR3. The first slider SB can slide along the direction of the third slide rail SR3, that is, the first slider SB can slide along the second direction E2. The temperature detection module 34 and the monofilament testing module 35 are disposed on the first slider SB. The control module 30 can control the moving apparatus 32 according to the temperature detection position data and the monofilament testing position data, so that the moving apparatus 32 moves the temperature detection module 34 to each temperature detection position via the sliding of the third slide rail SR3 and the sliding of the first slider SB, and the moving apparatus 32 moves the monofilament testing module 35 to each monofilament testing position, but not limited to this in actual implementation. The moving apparatus 32 may be an electric XYZ table or other types of electric multi-axis tables, which is not particularly limited in the present invention.

Figure 6:
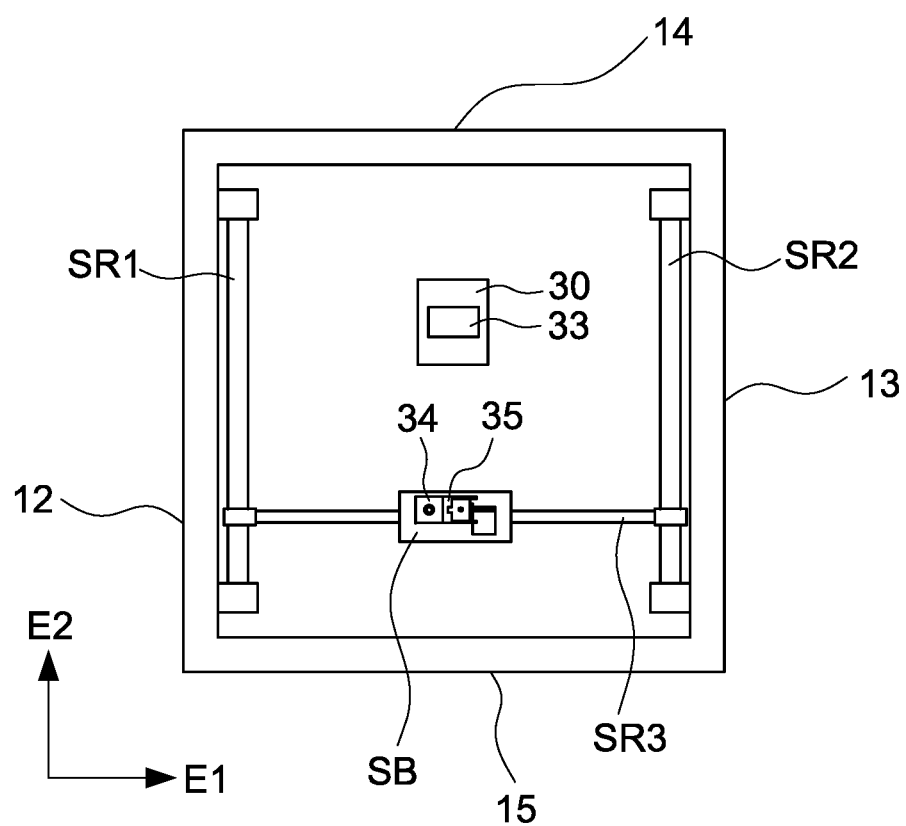
FIG. 6 is a schematic top view of the moving apparatus, the temperature detection module, the monofilament testing module and the image capture module inside the box of the foot data collection device according to another embodiment of the present invention.

Referring to FIG. 5, FIG. 6 and FIG. 7, in one embodiment of the present invention, the image capture module 33 is a miniature camera. The image capture module 33 is disposed on the inner surface of the back plate 11 of the box 1, and is located at a position near the center of the corresponding transparent plate 100, preferably at a position corresponding to the center of the transparent plate 100. Thus, when the user places the sole of the foot on the outer surface of the transparent plate 100, the image capture module 33 captures an optical image of the sole of the user's foot to obtain image data, and transmits the image data to the control module 30.

Referring to FIG. 5, FIG. 6 and FIG. 7, in one embodiment of the present invention, the temperature detection module 34 is an infrared thermograph. After the temperature detection module 34 reaches each temperature detection position, it will capture infrared images towards the sole of the user's foot, and record the temperature and the current temperature detection position to obtain temperature data.

Figure 8:
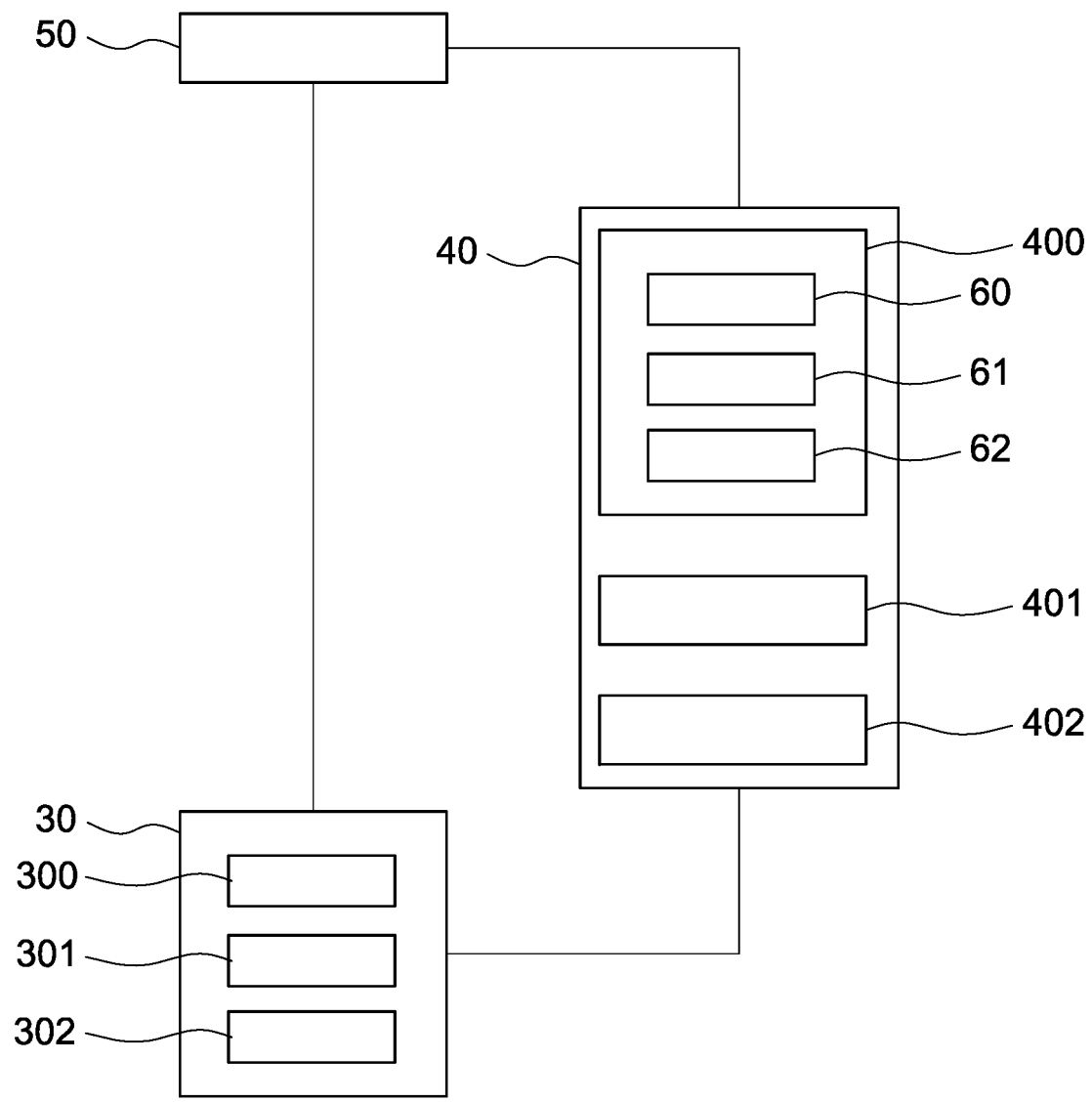
FIG. 8 is a schematic diagram of the control module, the external device and the cloud server according to one embodiment.

Referring to FIG. 7 and FIG. 8, the control module 30 includes a processor 300, a storage module 301, and a first transmission module 302. The processor 300 is configured to receive and transmit data, such as the image data, the temperature data, and the monofilament testing data, and to control the moving apparatus 32, the image capture module 33, the temperature detection module 34 and the monofilament testing module 35 that are coupled to the control module 30. The storage module 301 is configured to store data, such as the image data, the temperature data, and the monofilament testing data received by the processor 300. The storage module 301 stores the temperature detection position data and the monofilament testing position data in advance for the processor 300 to extract the image data, the temperature data, the monofilament testing data, the temperature detection position data and the monofilament testing position data stored in the storage module 301. The processor 300 can communicate with an external device 40 or a cloud server 50 via the first transmission module 302, so as to transmit data, such as the image data, the temperature data and the monofilament testing data, to the external device 40 or the cloud server 50. In one embodiment of the present invention, the processor 300 is a data processor, such as a central processing unit, a microprocessor, or a microcontroller. In one embodiment of the present invention, the storage module 301 is a volatile memory or a non-volatile memory. In one embodiment of the present invention, the first transmission module 302 is a wireless transmission module, such as a Bluetooth module, a Wi-Fi module or a mobile network module (such as 3G, 4G, 5G).

Figure 9:
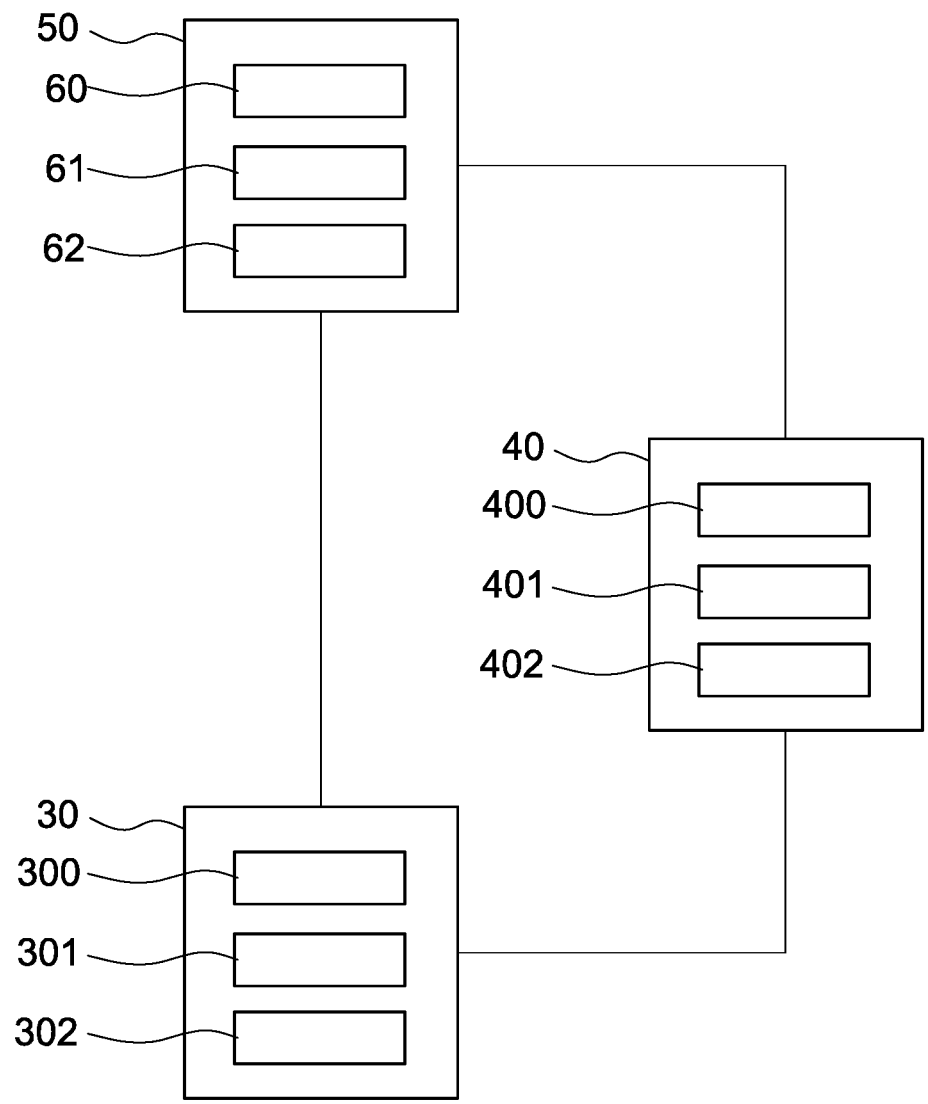
FIG. 9 is a schematic diagram of the control module, the external device and the cloud server according to another embodiment.
Figure 10:
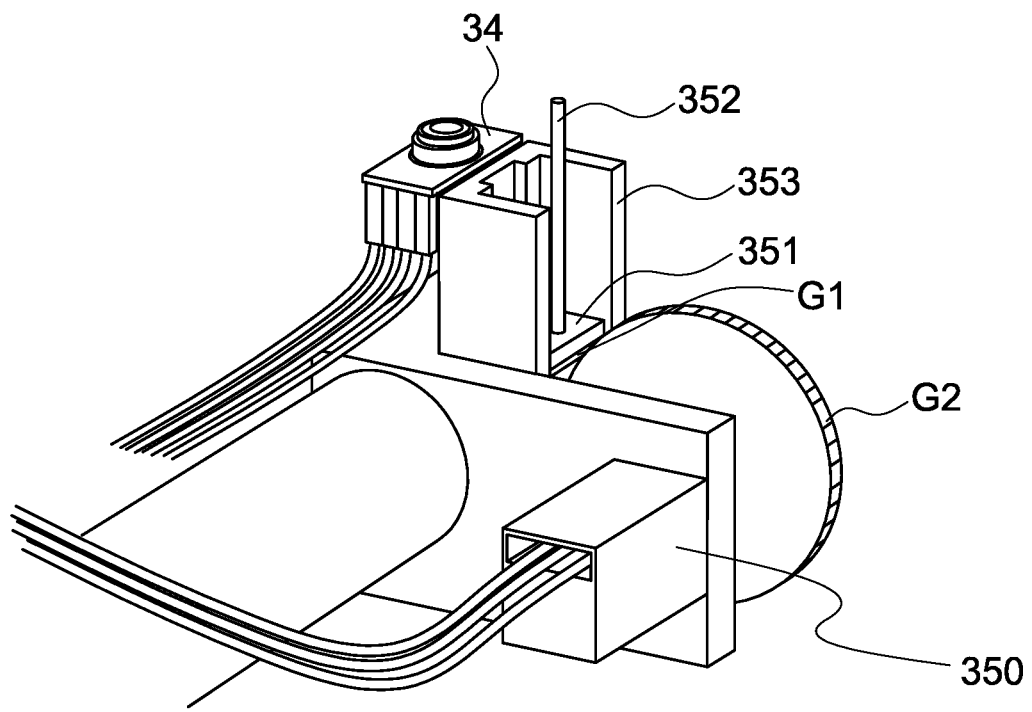
FIG. 10 is a perspective view of the monofilament testing module according to one embodiment.

Referring to FIG. 8 and FIG. 9, the external device 40 is configured to interact with the sole data collection device and the cloud server 50. The external device 40 can control the sole data collection device. The external device 40 can receive data, such as the image data, the temperature data and the monofilament testing data transmitted by the sole data collection device, and can display data, such as the image data, the temperature data and the monofilament testing data. In addition, the external device 40 can transmit data, such as the image data, the temperature data and the monofilament testing data, to the cloud server 50, and the cloud server 50 can extract data, such as the image data, the temperature data and the monofilament testing data, but not limited to this in actual implementation. The control module 30 can transmit data, such as the image data, the temperature data and the monofilament testing data to the external device 40 and cloud server 50 synchronously, or, the control module 30 can transmit data, such as the image data, the temperature data and the monofilament testing data, to the external device 40, and then the cloud server 50 can extract data, such as the image data, the temperature data and the monofilament testing data. The user's caregiver or relevant medical care personnel can extract data, such as the image data, the temperature data and the monofilament testing data, via the cloud server 50 to monitor the user's plantar conditions and determine whether to notify the user to go to a medical institution for a more detailed inspection to confirm whether the user has a diabetic foot. In one embodiment of the present invention, the external device 40 is a computing device with a display module 402, such as a desktop computer, a notebook computer, a tablet computer, or a smart phone.

Referring to FIG. 8 and FIG. 9, the external device 40 includes an application program 400, a second transmission module 401, and a display module 402. The external device 40 can interact with the sole data collection device and the cloud server 50 via the application program 400. The external device 40 can control the sole data collection device via the application program 400. The external device 40 can communicate with the sole data collection device via the second transmission module 401 to receive the image data, the temperature data and the monofilament testing data transmitted by the sole data collection device, and the display module 402 displays the image data, the temperature data and the monofilament testing data. In addition, the external device 40 can transmit data, such as the image data, the temperature data and the monofilament testing data, to the cloud server 50 via the second transmission module 401, and send a data extraction request to the cloud server 50 via the application program 400, and receive data, such as the image data, the temperature data and the monofilament testing data, transmitted by the cloud server 50 via the second transmission module 401. In one embodiment of the present invention, the second transmission module 402 is a wireless transmission module, such as a Bluetooth module, a Wi-Fi module or a mobile network module (such as 3G, 4G, 5G).

Referring to FIG. 7 and FIG. 8, in one embodiment of the present invention, an image analysis module 60 and a comparison analysis module 61 are stored in the application program 400 of the external device 40. The image analysis module 60 is configured to identify whether the image data includes a wound image. If the identified image data includes the wound image, the area where the wound image in the image data is marked to obtain image analysis result data. If the identified image data does not include the wound image, the image data serves as the image analysis result data. In an embodiment of the present invention, the image analysis module 60 marks the area where the wound image in the image data is located by object detection, that is, the area of the wound image is marked with a rectangular frame and the area within the rectangular frame is the marked area. The comparison analysis module 61 compares the image analysis result data and the monofilament testing position data to determine whether each monofilament testing position overlaps with the marked area, that is, to convert the marked area into the coordinate range corresponding to the aforementioned virtual coordinate plane to form a marked area coordinate range, and to compare whether the marked area coordinate range covers any monofilament testing position. If the marked area coordinate range covers at least one monofilament testing position, it is determined to be overlapped. If it is determined that there is an overlap, skip testing message data will be generated, and the skip testing message data will be transmitted to the control module 30.

The skip testing message data is to instruct the control module 30 to control the moving apparatus 32 to skip the monofilament testing position overlapping with the marked area, so as to avoid a further injury to the user's plantar wound by performing monofilament testing on the user's plantar wound.

Referring to FIG. 7 and FIG. 9, in another embodiment of the present invention, the image analysis module 60 and the comparison analysis module 61 are stored in the cloud server 50. The image data may be transmitted to the cloud server 50 via the control module 30 or the external device 40. The monofilament testing position data may be stored in the cloud server 50 in advance, or may be transmitted to the cloud server 50 via the control module 30 or the external device 40. The cloud server 50 uses the image analysis module 60 to analyze the image data to obtain image analysis result data. The comparison analysis module 61 compares the image analysis result data and the monofilament testing position data to determine whether each monofilament testing position overlaps with the marked area. If it is determined that there is an overlap, skip testing message data will be generated, and the skip testing message data will be transmitted to the control module 30; or the skip testing message data will be first transmitted to the external device 40, and then the skip testing message data will be transmitted to the control module 30 via the external device 40.

Referring to FIG. 8 and FIG. 9, in one embodiment of the present invention, the image analysis module 60 is a trained convolutional neural network model. In order to train the convolutional neural network model to identify whether the image data includes a wound image and to mark the area where the wound image is located to generate image analysis result data, firstly, multiple healthy sole image data and multiple sole wound image data are obtained through a medical database (for example, a hospital database), and each sole wound image data is marked by object detection to form sole wound image marked data. Next, the healthy sole image data and the sole wound image marked data are generated in batches for image analysis training set, so as to train the convolutional neural network model to improve the accuracy of image analysis and minimize the loss function. Finally, the trained convolutional neural network model can be obtained. But, the actual implementation is not limited to this. The image analysis module 60 is not limited to a convolutional neural network model. It may be a machine learning model, such as a recurrent neural network model or a Long short-term memory (LSTM) model.

Referring to FIG. 8 and FIG. 9, in one embodiment of the present invention, the comparison analysis module 61 is another trained convolutional neural network model. In order to train another convolutional neural network model to compare the image analysis result data and the monofilament testing position data to determine whether each monofilament testing position overlaps with the marked area, the healthy sole image data and the sole wound image marked data are generated in batches for comparison analysis training set and compared with the monofilament testing position data to determine whether each monofilament testing position overlaps with the marked area. If it is determined that there is overlap, skip testing message data will be generated, so as to obtain another trained convolutional neural network model. But, the actual implementation is not limited to this. The comparison analysis module 61 is not limited to a convolutional neural network model. It may be a machine learning model, such as a recurrent neural network model or a long short-term memory (LSTM) model.

Referring to FIG. 8 and FIG. 9, in another embodiment of the present invention, the application program 400 in the external device 40 further includes a temperature comparison module 62. The temperature comparison module 62 is configured to compare each temperature data. If the recorded temperature difference in any two of the temperature data is greater than 2.2° C., the application program 400 will generate temperature warning data and transmit the temperature warning data to the cloud server 50, but not limited to this in actual implementation. The temperature comparison module 62 may be stored in the cloud server 50. If the temperature comparison module 62 generates a temperature warning message after comparing each temperature data, the cloud server 50 will transmit the temperature warning message to the external device 40.

Referring to FIG. 1, FIG. 5, FIG. 6 and FIG. 10, in one embodiment of the present invention, the monofilament testing module 35 includes a third motor 350, a second slider 351, a monofilament 352, and a fourth slide rail 353. A gear G1 is provided on the third motor 350. The second slider 351 is arranged on the fourth slide rail 353. One end of the monofilament 352 is connected to one end of the second slider 351 facing the data collection plate 10. A rack G2 is provided on one side of the second slider 351 facing the gear G1. The gear G1 is meshed with the rack G2. The fourth slide rail 353 is perpendicular to the data collection plate 10. The other end of the monofilament 352 is also perpendicular to the data collection plate 10. When the third motor 350 rotates the gear G1, the gear G1 will drive the rack G2 to move the second slider 351 along the fourth slide rail 353, so that the other end of the monofilament 352 stretches out to perform monofilament testing for the user's sole. The monofilament 352 is retraced after completing the monofilament testing. The monofilament 352 is a 10 g single strand of nylon. The monofilament testing is that the other end of the monofilament 352 is placed at 90 degrees to the sole of the user's foot, thereby stimulating the sole of the user's foot. In one embodiment of the present invention, the third motor 350 is a servo motor, but not limited to this in actual implementation. It may be different types of motors, such as DC motors, AC motors, or stepping motors.

Figure 11:
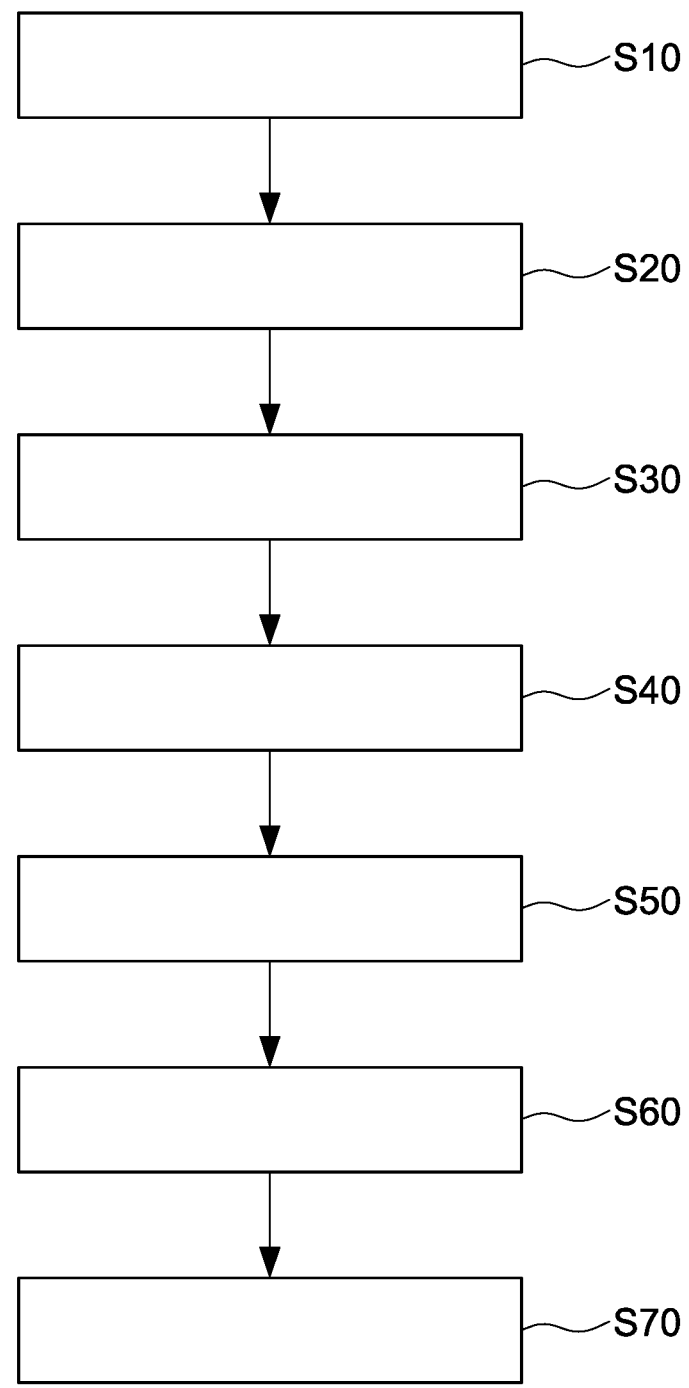
FIG. 11 is a flow diagram of the sole data collection method according to one embodiment.

Referring to FIG. 11, the present invention provides a sole data collection method, comprising a device providing step S10, an image capturing step S20, an image analysis step S30, a comparison analysis step S40, a temperature detection step S50, a monofilament testing step S60, and an inquiry reply step S70. The steps are described below.

Referring to FIG. 11, in the device providing step S10, the aforementioned sole data collection device is provided.

Referring to FIG. 5, FIG. 7, FIG. 8, FIG. 9 and FIG. 11, in image capturing step S20, the image capture module 33 captures sole images to obtain image data and transmits the image data to the control module 30. In one embodiment of the present invention, the user places the sole of one foot on the outer surface of the data collection plate 10 of the sole data collection device, and the image capture module 33 captures images of the sole of the user's foot to obtain the image data and transmit the image data to the processor 300 of the control module 30. Then, the processor 300 transmits the image data to the storage module 301 for storage. In one embodiment of the present invention, the user places the soles of both feet on the outer surface of the transparent plate 100 of the data collection plate 10 of the sole data collection device, and the image capture module 33 captures images of the soles of the user's feet to obtain the image data, but not limited to this in actual implementation. The image capture module 33 may capture respective images of the sole of the user's left foot and the sole of the user's right foot to obtain the image data.

Referring to FIG. 8, FIG. 9 and FIG. 11, in the image analysis step S30, the control module 30 transmits the image data to the image analysis module 60 for analysis to identify whether the image data includes a wound image. If the identified image data includes the wound image, the area where the wound image in the image data is located is marked to obtain image analysis result data. If the identified image data does not include the wound image, the image data serves as the image analysis result data. In one embodiment of the present invention, the image analysis module 60 is stored in the application program 400 of the external device 40. Therefore, after the image analysis module 60 transmits the image data to the processor 300, the processor 300 transmits the image data to the external device 40 via the first transmission module 302. Then, the image analysis module 60 of the application program 400 of the external device 40 analyzes the image data to identify whether the image data includes a wound image. If the identified image data includes the wound image, the area where the wound image in the image data is located is marked. If the identified image data does not include the wound image, the image data serves as the image analysis result data. For example, the image analysis module 60 identifies and marks, in the image data, a wound image corresponding in position to the first metatarsal bone of the left foot and another wound image corresponding in position to the third metatarsal bone of the left foot. The area where the wound image in the image data is located is marked by object detection, that is, the area of the wound image is marked with a rectangular frame and the area within the rectangular frame is the marked area. But, the actual implementation is not limited to this. The image analysis module 60 may be stored in the cloud server 50. The control module 30 directly transmits the image data to the cloud server 50, or, the control module 30 transmits the image data to the external device 40 first, and then the external device 40 transmits the image data to the cloud server 50.

Referring to FIG. 1, FIG. 7, FIG. 8, FIG. 9 and FIG. 11, in the comparison and analysis step S40, the image analysis module 60 transmits the image analysis result data to the comparison analysis module 61. The comparison analysis module 61 compares the image analysis result data and the monofilament testing position data to determine whether each monofilament testing position overlaps with the marked area. If it is determined that there is an overlap, skip testing message data will be generated, and the skip testing message data will be transmitted to the control module 30. In one embodiment of the present invention, the comparison analysis module 61 is stored in the application program 400 of the external device 40. After the image analysis module 60 transmits the image analysis result data to the comparison analysis module 61, the comparison analysis module 61 compares the image analysis result data and the monofilament testing position data to determine whether each monofilament testing position overlaps with the marked area. If it is determined that there is an overlap, skip testing message data will be generated, and the skip testing message data will be transmitted to the control module 30. The skip testing message data is to instruct the control module 30 to control the moving apparatus 32 to skip the monofilament testing position that overlaps with the marked area, so as to avoid a further injury to the user's plantar wound by performing monofilament testing on the user's plantar wound. For example, the image analysis result data has the marked area corresponding to the position of the first metatarsal bone of the left foot and the position of the third metatarsal bone corresponding to the left foot, and the marked area overlaps with the monofilament testing position corresponding to the second opening H2, but the marked area does not overlap with the monofilament testing position corresponding to the third opening H3. Because it is determined that the marked area overlaps with the monofilament testing position corresponding to the second opening H2, skip testing message data is generated, and the skip testing message data is transmitted to the control module 30 via the second transmission module 401. The skip testing message data is to instruct the moving apparatus 32 to skip the monofilament testing position corresponding to the second opening H2. Therefore, when the moving apparatus 32 moves the monofilament testing module 35, it will move the monofilament testing module 35 only to the monofilament testing positions corresponding to the first opening H1, the third opening H3, the fourth opening H4, the seventh opening H7, the eighth opening H8, the ninth opening H9 and the tenth opening H10. But the actual implementation is not limited to this. The comparison analysis module 61 and the image analysis module 60 may be stored in the cloud server 50. The monofilament testing position data may be stored in the cloud server 50 in advance or transmitted to the cloud server 50 via the external device 40. Therefore, after the image analysis result data obtained by the image analysis module 60 is transmitted to the comparison analysis module 61, the comparison analysis module 61 will compare the image analysis result data and the monofilament testing position data. If the skip testing message data is generated, the skip testing message data will be transmitted to the control module 30. The cloud server 50 can directly transmit the skip testing message data to the control module 30, or, the cloud server 50 transmits the skip testing message data to the external device 40 first, and then the external device 40 transmits the skip testing message data to the control module 30.

Referring to FIG. 1, FIG. 7, FIG. 8, FIG. 9 and FIG. 11, in the temperature detection step S50, the control module 30 controls the moving apparatus 32 to move the temperature detection module 34 to each temperature detection position according to the temperature detection position data. The temperature detection module 34 performs temperature detection at each temperature detection position to obtain corresponding temperature data. Then, the temperature data is transmitted to the control module 30, and the control module 30 transmits the temperature data to the external device 40 or the cloud server 50. In one embodiment of the present invention, the user places the sole of the foot on the outer surface of the data collection plate 10, corresponding to the positions of the plurality of openings. The control module 30 controls the moving apparatus 32 according to the temperature detection position data for the temperature detection module 34 to move to the temperature detection positions corresponding to the first opening H1, the second opening H2, the third opening H3, the fourth opening H4, the fifth opening H5, the sixth opening H6, the seventh opening H7, the eighth opening H8, the ninth opening H9, the tenth opening H10, the eleventh opening H11 and the twelfth opening H12. After the temperature detection module 34 reaches each temperature detection position, it will perform temperature detection to obtain the temperature data. For example, the temperature detection module 34 is an infrared thermograph. The temperature detection is to capture infrared images of the user's soles, and record the temperature and the current temperature detection position to obtain the temperature data. When the temperature detection module 34 is moved to the temperature detection position corresponding to the second opening H2 that corresponds in position to the first metatarsal bone of the user's left foot, the temperature detection module 34 will capture infrared images of the position corresponding to the first metatarsal bone of the user's left foot, and record the temperature (such as, 30.7° C.) and the temperature detection position corresponding to the second opening H2, so as to obtain the temperature data. The temperature data is transmitted to the control module 30. The control module 30 may transmit the temperature data to the external device first, and then the external device 40 transmits the temperature data to the cloud server 50. But, the actual implementation is not limited to this. The control module 30 can transmit the temperature data to the external device 40 and cloud server 50 synchronously. In addition, the control module 30 may transmit the temperature data to the cloud server 50 first, and then the external device 40 extracts the temperature data via the cloud server 50.

Referring to FIG. 1, FIG. 7, FIG. 8, FIG. 9 and FIG. 11, in the monofilament testing step S60, the control module 30 controls the moving apparatus 32 to move the monofilament testing module 35 to each monofilament testing position according to the monofilament testing position data. The monofilament testing module 35 performs monofilament testing at each monofilament testing position. After the monofilament testing is completed, the control module 30 will record the current monofilament testing position to obtain the corresponding monofilament testing data. Then, the control module transmits the corresponding monofilament testing data to the external device 40 or the cloud server 50. If the control module 30 receives the skip testing message data, it will control the moving apparatus 32 to skip the monofilament testing position overlapping with the marked area. In one embodiment of the present invention, the user places the sole of the foot on the outer surface of the data collection plate 10, corresponding to the positions of the plurality of openings. The control module 30 controls the movement of the moving apparatus 32 according to the monofilament testing position data and the skip testing message data. The skip testing message data is to instruct the moving apparatus 32 to skip the monofilament testing position corresponding to the second opening H2. Therefore, the control module 30 controls the movement of the moving apparatus 32, so that the monofilament testing module 35 is moved to the monofilament testing positions corresponding to the first opening H1, the third opening H3, the fourth opening H4, the seventh opening H7, the eighth opening H8, the ninth opening H9 and the tenth opening H10. After the monofilament testing module 35 reaches each monofilament testing position, the monofilament testing module 35 will perform monofilament testing. The monofilament testing is that the monofilament 352 vertically passes through the corresponding opening and is placed at 90 degrees to the sole of the user's foot, thereby stimulating the sole of the user's foot. The monofilament 352 is returned after the monofilament testing is completed. After completing the monofilament testing, the control module 30 will record the current monofilament testing position to obtain the corresponding monofilament testing data. The control module 30 transmits the corresponding monofilament testing data to the external device 40, and then the external device 40 transmits the corresponding monofilament testing data to the cloud server 50. For example, when the monofilament testing module 35 is moved to the position corresponding to the third opening H3, the monofilament testing module 35 will perform monofilament testing. The monofilament testing is that the monofilament 352 vertically passes through the third opening H3 and is placed at 90 degrees to the sole of the user's foot. Because the third opening H3 corresponds in position to the third metatarsal bone of the user's left foot, the monofilament 352 will cause stimulation to the third metatarsal bone of the user's left foot. The monofilament 352 is returned after the monofilament testing is completed. After completing the monofilament testing, the control module 30 will record the current monofilament testing position to obtain the corresponding monofilament testing data. The control module 30 transmits the corresponding monofilament testing data to the external device 40, and then the external device 40 transmits the corresponding monofilament testing data to the cloud server 50. But, the actual implementation is not limited to this. The control module 30 may transmit the temperature data to the external device 40 and the cloud server 50 synchronously. In addition, the control module 30 may transmit the monofilament testing data to the cloud server 50 first, and then the external device 40 extracts the monofilament testing data from the cloud server 50.

Referring to FIG. 8, FIG. 9 and FIG. 11, in the inquiry reply step S70, after the external device 40 receives the monofilament testing data, it will generate corresponding inquiry message data and display the inquiry message data on the external device 40. After that, the external device 40 replies to the inquiry message data to obtain corresponding reply message data, and then the external device 40 transmits the reply message data to the cloud server 50. In one embodiment of the present invention, the inquiry message data is to inquire the user's plantar sensation. The inquiry message data may be in the form of text or pictures, for example, a text message "Do you have any sensation on the sole of the foot?" or "Which area of the sole of the foot can you sense?", and the inquiry message data will be displayed on the display module 402 of the external device 40. The user can reply the inquiry message data via the external device 40 to obtain the corresponding reply message data. Then, the external device 40 transmits the reply message data to the cloud server 50, so that the user's caregiver or relevant medical care personnel can extract the reply message data via the cloud server 50. For example, the external device 40 is a smart phone. The monofilament testing module 35 is moved to the monofilament testing position corresponding to the third opening H3 to complete monofilament testing. After the control module 30 obtains the corresponding monofilament testing data, the control module 30 will transmit the monofilament testing data to the external device 40. The application program 400 of the external device 40 will generate the corresponding inquiry message data, and the inquiry message data is displayed on the display module 402, that is, the screen of the smart phone. The inquiry message data is "Do you have any sensation on the sole of the foot?", and it provides the choice of option input or text input. The option input provides "Yes" and "No" checkbox for the user to reply to the inquiry message data. If the user does not have any sensation on the sole of the foot, he/she can enter "no sensation" on the virtual keyboard of the smart phone, or touch the checkbox corresponding to "No" to generate the reply message data. Then, the external device 40 transmits the reply message data to the cloud server 50 via the second transmission module 401.

Figure 12:
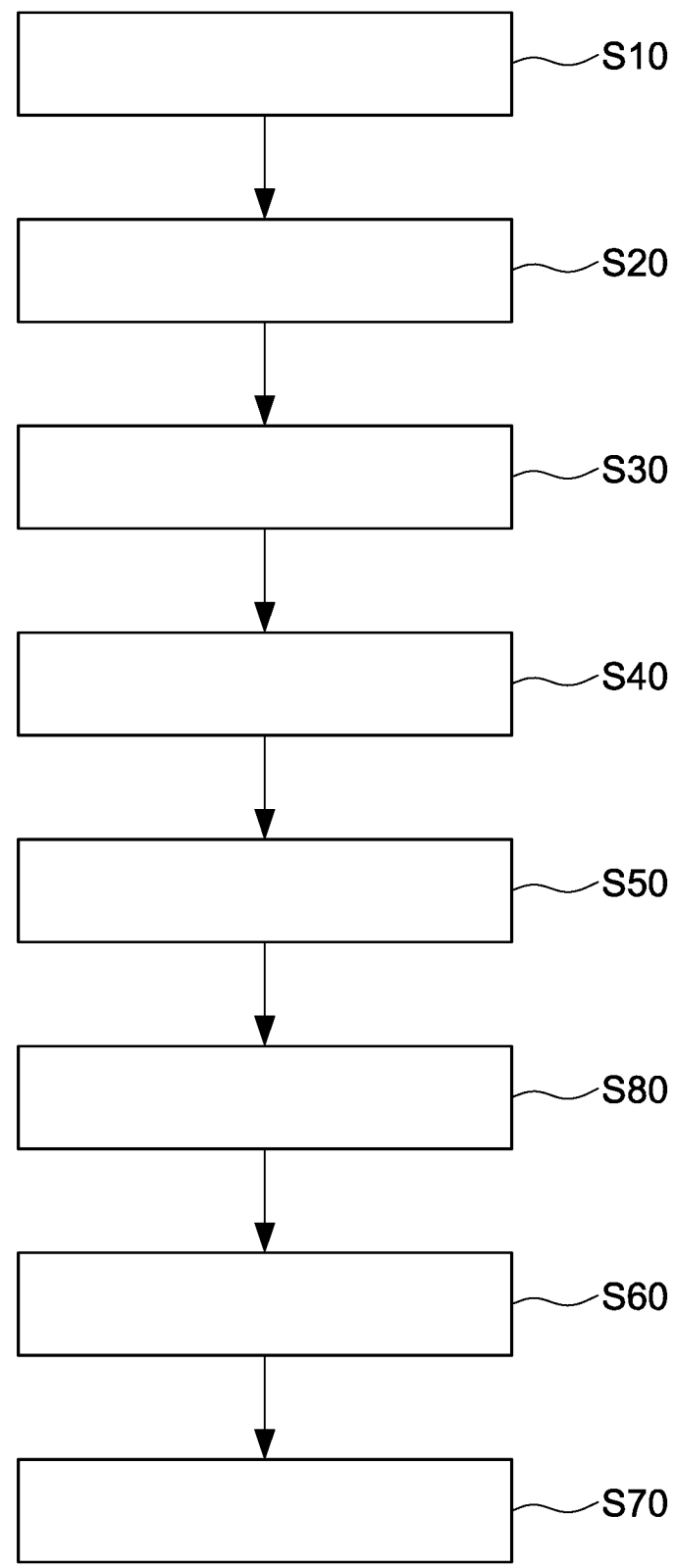
FIG. 12 is a flow diagram of the sole data collection method according to another embodiment.

Referring to FIG. 8, FIG. 9 and FIG. 12, in one embodiment of the present invention, the sole data collection method of the present invention further comprises a temperature comparison step S80 after the temperature detection step S50. In the temperature comparison step S80, the temperature comparison module 62 compares each temperature data. If the temperature difference recorded in any two of the temperature data is greater than 2.2° C., temperature warning data will be generated. In one embodiment of the present invention, the temperature comparison module 62 is a preset comparison function program. The temperature comparison module 62 is stored in the application program 400 of the external device 40. When the temperature comparison module 62 finds that the absolute value of the subtraction of the temperature values recorded in any two of the temperature data is greater than 2.2, it will generate the temperature warning data. The unit of temperature mentioned is "° C.". The temperature warning data warns the user that the sole of the foot may be inflamed. The temperature warning data may be presented in the form of text description or color marking. The temperature warning data may be displayed on the display module 402 of the external device 40, for example, it may be a text description of "abnormal temperature", or it displays the abnormal temperature value in red. The temperature warning data will be transmitted to the cloud server 50 via the second transmission module 401 of the external device 40. But, the actual implementation is not limited to this. The temperature comparison module 62 may be stored in the cloud server 50. If the temperature comparison module 62 generates a temperature warning message after comparing each temperature data, the cloud server 50 will transmit the temperature warning message to the external device 40.

Referring to FIG. 8, and FIG. 9, after completing the sole data collection method, the user's caregiver and relevant medical care personnel can extract the image data, the temperature data, the monofilament testing data, the reply message data or the temperature warning data via the cloud server 50, so as to monitor the user's plantar conditions and determine whether to notify the user to go to a medical institution for a more detailed inspection to confirm whether the user is diabetic feet.

To sum up, the sole data collection device and the sole data collection method provided by the present invention are not only convenient for users to collect sole data at home at any time, but also allow the user's caregiver and/or relevant medical care personnel to continuously monitor the user's plantar conditions. The present invention solves the problem that it is time-consuming to go to a medical institution for relevant examinations and cannot be screened immediately.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A sole data collection device, comprising a box, the box including a data collection plate and a back plate, the data collection plate being arranged correspondingly to the back plate; the data collection plate including a transparent plate and a plurality of openings, the plurality of openings being arranged on the data collection plate and corresponding in position to a great toe, a first metatarsal bone, a third metatarsal bone, a fifth metatarsal bone, a midfoot and a heel of a left foot and a right foot of a user; the box including a control module, a power supply module, a moving apparatus, an image capture module, a temperature detection module and a monofilament testing module therein, the control module being coupled to the power supply module, the moving apparatus, the image capture module, the temperature detection module and the monofilament testing module; temperature detection position data and monofilament testing position data being stored in the control module in advance; the control module being configured to communicate with an external device a cloud server; the image capture module being arranged on an inner surface of the back plate of the box and corresponding in position to the transparent plate; the moving apparatus being arranged on an inner surface of the box, the temperature detection module and the monofilament testing module being arranged on the moving apparatus, the control module controlling the moving apparatus to move the temperature detection module and the monofilament testing module according to the temperature detection position data and the monofilament testing position data.

2. The sole data collection device as claimed in claim 1, further comprising a support handle, the support handle including a first rod, a second rod and a third rod, one end of the first rod being rotatably connected to one side of the box, one end of the second rod being rotatably connected to another side of the box, one end of the third rod being fixedly connected to another end of the first rod, another end of the third rod being fixedly connected to another end of the second rod, wherein when the third rod is located between an outer surface of the back plate of the box and a ground and one side of the third rod is in contact with the ground, an included angle is defined between an imaginary plane parallel to the data collection plate and the ground, and the included angle is 15-35 degrees.

3. The sole data collection device as claimed in claim 2, wherein a first holding member is provided on the one side of the box, and the first holding member is located on a rotation path of the first rod; a second holding member is provided on the another side of the box, and the second holding member is located on a rotation path of the second rod; wherein when the first rod is held by the first holding member, the second rod is held by the second holding member, and the one side of the third rod is in contact with the ground, the included angle is defined between the imaginary plane and the ground.

4. The sole data collection device as claimed in claim 1, wherein when the back plate is in contact with the ground, an included angle is defined between an imaginary plane parallel to the data collection plate and the ground, and the included angle is 15-35 degrees.

5. The sole data collection device as claimed in claim 1, wherein the monofilament testing module includes a third motor, a second slider, a monofilament and a fourth slide rail, a gear is provided on the third motor, the second slider is arranged on the fourth slide rail, one end of the monofilament is connected to one end of the second slider facing the data collection plate, a rack is provided on one side of the second slider facing the gear, the gear is meshed with the rack, the fourth slide rail is perpendicular to the data collection plate, and another end of the monofilament is perpendicular to the data collection plate.

6. The sole data collection device as claimed in claim 1, wherein the control module includes a processor, a storage module and a first transmission module, wherein the processor is configured to receive and transmit the data transmitted by the image capture module, the temperature detection module and the monofilament testing module and to control the moving apparatus, the image capture module, the temperature detection module and the monofilament testing module, wherein the storage module is configured to store the data received by the processor, and the storage module stores the temperature detection position data and the monofilament testing position data in advance for the processor to extract the data stored in the storage module.

7. The sole data collection device as claimed in claim 1, wherein the external device includes an application program, a second transmission module and a display module, the external device interacts with the sole data collection device and the cloud server via the application program, the external device controls the sole data collection device via the application program, the external device communicates with the sole data collection device and the cloud server via the second transmission module to receive the data transmitted by the sole data collection device or the cloud server, or to transmit data to the sole data collection device or the cloud server; the display module is configured to display the data in the external device.

8. A sole data collection method, comprising:
- a device providing step: providing the sole data collection device as claimed in claim 1;
- an image capturing step: the image capture module capturing a sole image to obtain image data and transmitting the image data to the control module;
- an image analysis step: the control module transmitting the image data to an image analysis module for analysis to identify whether the image data includes a wound image, if the identified image data includes the wound image, the area where the wound image in the image data is located being marked to obtain image analysis result data; if the identified image data does not include the wound image, the image data serving as the image analysis result data;
- a comparison analysis step: the image analysis module transmitting the image analysis result data to a comparison analysis module, the comparison analysis module comparing the image analysis result data and the monofilament testing position data to determine whether each monofilament testing position overlaps with the marked area, if it is determined that there is an overlap, skip testing message data being generated and the skip testing message data being transmitted to the control module;
- a temperature detection step: the control module controlling the moving apparatus to move the temperature detection module to each temperature detection position according to the temperature detection position data, the temperature detection module performing temperature detection at each temperature detection position to obtain corresponding temperature data, the corresponding temperature data being transmitted to the control module, the control module transmitting the corresponding temperature data to the external device or the cloud server;
- a monofilament testing step: the control module controlling the moving apparatus to move the monofilament testing module to each monofilament testing position according to the monofilament testing position data, the monofilament testing module performing monofilament testing at each monofilament testing position, after completing the monofilament testing, the control module recording the current monofilament testing position to obtain corresponding monofilament testing data, the control module transmitting the corresponding monofilament testing data to the external device or the cloud server; wherein if the control module receives the skip testing message data, the control module controls the moving apparatus to skip the monofilament testing position overlapping with the marked area;
- an inquiry reply step, after receiving the corresponding monofilament testing data, the external device generating corresponding inquiry message data and displaying the inquiry message data on the external device, the external device replying to the inquiry message data to obtain corresponding reply message data, the external device transmitting the reply message data to the cloud server, wherein the inquiry message data is to inquire the user's plantar sensation; wherein the image analysis module is stored in the external device or the cloud server; wherein the comparison analysis module is stored in the external device or the cloud server.

9. The sole data collection method as claimed in claim 8, wherein the skip testing message data is to instruct the control module to control the moving apparatus to skip the monofilament testing position overlapping with the marked area.

10. The sole data collection method as claimed in claim 8, further comprising a temperature comparison step after the temperature detection step, in the temperature comparison step, the temperature comparison module comparing each of the temperature data, if a temperature difference recorded in any two of the temperature data is greater than 2.2° C., temperature warning data being generated, wherein the temperature comparison module is stored in the external device or the cloud server.

* * * * *